United States Patent [19]

Popp

[11] Patent Number: 5,433,950
[45] Date of Patent: Jul. 18, 1995

[54] FLEXIBLE COLLODION COMPOSITIONS

[75] Inventor: Karl F. Popp, Schodack Landing, N.Y.

[73] Assignee: Schering-Plough Healthcare Products, Inc., Memphis, Tenn.

[21] Appl. No.: 48,818

[22] Filed: Apr. 16, 1993

Related U.S. Application Data

[63] Continuation-in-part of Ser. No. 724,824, Jul. 2, 1991, abandoned, which is a continuation-in-part of Ser. No. 649,692, Feb. 1, 1991, abandoned, which is a continuation-in-part of Ser. No. 520,374, May 7, 1990, abandoned.

[51] Int. Cl.$^6$ .................. A61K 47/38; A61K 47/32
[52] U.S. Cl. .................. 424/400; 514/772.4; 514/772.6; 514/781; 424/407
[58] Field of Search .......... 424/61, 486–488; 514/772.4, 772.6, 781; 524/32; 106/195

[56] References Cited

U.S. PATENT DOCUMENTS

| | | | |
|---|---|---|---|
| 3,615,792 | 10/1971 | Keene | 106/170 |
| 4,055,660 | 10/1977 | Meierhenry | 424/310 |
| 4,179,304 | 12/1979 | Rossomando | 106/177 |
| 4,563,473 | 1/1986 | Hofman et al. | 514/399 |
| 4,588,590 | 5/1986 | Bernstein | 424/61 |
| 4,681,635 | 7/1987 | Stiefel et al. | 106/178 |
| 4,778,786 | 10/1988 | Reever et al. | 514/54 |
| 4,814,015 | 3/1989 | Quinlan | 106/170 |
| 4,863,970 | 9/1989 | Patel et al. | 514/784 |
| 4,888,354 | 12/1989 | Chang et al. | 514/424 |
| 4,895,727 | 1/1990 | Allen | 424/642 |
| 4,957,730 | 9/1990 | Bohn et al. | 424/61 |

OTHER PUBLICATIONS

Oneto et al., *Chem. Abstracts* 89:30604e, vol. 89, p. 392 (1978).
Materne et al., *Chem. Abstracts* 95:68058s, vol. 95, p. 393 (1981).
Heller et al., *Chem. Abstracts*, 102:119631w, vol. 102, p. 400 (1985).
Neumüller, *Rompp's Chemistry Dictionary*, 7th Ed., p. 676, Franckh'sche Verlagshandlung, Stuttgart (with translation).

*Primary Examiner*—Edward J. Webman
*Attorney, Agent, or Firm*—Mathews, Woodbridge & Collins

[57] ABSTRACT

Film-forming flexible collodion compositions can be improved by including one or more topically acceptable polymers in an amount sufficient to increase the resilience of the film formed. Suitable polymers include polyalkylenes and (meth)acrylate homo- or copolymers. The compositions can further include salicylic acid and a topically acceptable crystallization inhibitor in an amount sufficient to suppress the crystallization of dissolved salicylic acid from the composition.

6 Claims, No Drawings

FLEXIBLE COLLODION COMPOSITIONS

CROSS-REFERENCE TO RELATED APPLICATIONS

This is a continuation-in-part of Ser. No. 07/724,824 filed Jul. 2, 1991 which in turn is a continuation-in-part of Ser. No. 07/649,692 filed Feb. 1, 1991 and Ser. No. 07/520,374 filed May 7, 1990, all abandoned.

DETAILED DESCRIPTION

The present invention pertains to improved film-forming flexible collodion compositions intended for topical application.

Flexible collodion typically consists of collodion containing 2% by weight of camphor and 3% by weight of castor oil. Collodion is a solution, typically 4 parts by weight of nitrocellulose dissolved in 75 parts by volume of ethyl ether and 25 parts by volume of ethanol. Flexible collodion is generally a pale yellow, syrupy liquid which, when applied to the skin and thus exposed to air, dries to form a colorless or nearly colorless flexible, adherent film.

Flexible collodion compositions are widely employed in human and veterinary applications. Although flexible collodion itself can be used as a skin protectant, various therapeutic agents often are added, as for example, salicylic acid, tannic acid, cantharides, camphor, etc.

Since the therapeutic use of flexible collodion preparations depends upon the formation of a protective film, the quality of the film which is obtained is important. The film formed by the flexible collodion composition should be resilient; i.e., it should be durable and resistant to "rub off" or abrasion, tenacious, flexible (that is, plastic), and occlusive.

The present invention is based upon the discovery that addition of one or more topically acceptable liquid or solid polymers increases the resilience of the film formed by a flexible collodion composition.

Typical polymers which can be used are polyalkylenes, (meth)acrylate homopolymers and (meth)acrylate copolymers. The use of "meth" as a prefix in parenthesis indicates, in accordance with common practice, that the polymer molecule is derived from monomers having the carbon atom skeleton of either or both of acrylic acid and methacrylic acid.

Suitable polyalkylenes include polybutylene and polyisoprene. Among the polyalkylenes polybutylene, a copolymer formed by the polymerization of isobutylene and butene, is preferred. Typically polybutylenes will have an average molecular weight of from about 300 to about 2000 and a viscosity index of from about 70 to about 122 (ASTM D2270). Various grades, corresponding to different average molecular weights, are commercially available from Amoco Chemical Company {Chicago, Ill.} under the name Indopol®. Thus by way of example only, Indopol L-50® has an average molecular weight of 420 and a viscosity index of about 90 when measured by ASTM D2270 whereas Indopol H-100® has an average molecular weight of 920 and a viscosity index of about 109. Suitable polybutylenes include:

| Polybutylenes | Ave. Mol Wt. | Viscosity Index |
| --- | --- | --- |
| Indopol L-14 ® | 320 | 69 |
| Indopol L-50 ® | 420 | 90 |
| Indopol L-100 ® | 460 | 95 |
| Indopol H-15 ® | 560 | 96 |
| Indopol H-25 ® | 610 | 97 |
| Indopol H-35 ® | 660 | 100 |
| Indopol H-50 ® | 750 | 104 |
| Indopol H-100 ® | 920 | 109 |
| Indopol H-300 ® | 1290 | 117 |
| Indopol H-1500 ® | 2060 | 122 |
| Indopol H-1900 ® | 2300 | 122 |

(Meth)acrylate homopolymers and copolymers are well-known polymeric substances characterized by the presence of same or different repeating structures of the formula:

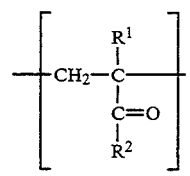

in which $R^1$ is hydrogen or methyl and $R^2$ is amino, hydroxy, methoxy or ethoxy which may be further unsubstituted or substituted.

Homopolymers include poly(acrylic acid) {$R^1$=H; $R^2$=OH}, poly(methyl methacrylate) {$R^1$=methyl; $R^2$=methoxy}, poly(ethyl methacrylate) {$R^1$=methyl; $R^2$=ethoxy}, polyacrylamide {$R^1$=H; $R^2$=NH$_2$}, and poly(ethyl acrylate) {$R^1$=H; $R^2$=ethoxy}, all of which are commercially available under various tradenames such as Acrysol A-1 ® {Rohm & Haas Co., Philadelphia, Pa.}, Lucite 4F ® {E. I. dupont de Nemours, Wilmington, Del.}, Gelamide 250 ® {American Cyanamid Co., Wayne, N.J.}, etc.

Copolymers include those in which the above unit of Formula I constitutes one comonomer unit and one or more units having a different structure constitutes another comonomer unit. The second structure can be a different structure of Formula I or can be a distinct polymerizable monomer. Representatives of the first type of copolymer include those of acrylic acid and an alkyl acrylate such as Carboset 915 ® {B. F. Goodrich, Brecksville, Ohio}, copolymers of acrylamide and acrylic acid such as Reten 423 ® {Hercules, In., Wilmington} (typically as the sodium salt), copolymers of acrylamide and an alkyl acrylate such as Ultrahold 8 ® {BASF Corporation, Parsippany, N.J.}, copolymers of alkyl acrylates and methacrylic acid or a salt thereof such as Rhoplex K-3 ® {Rohm & Haas Co., Philadelphia, Pa.}, copolymers of ethyl methacrylate, abietyl methacrylate, and diethylaminoethyl methacrylate which are quaternized with dimethyl sulfate, copolymers of ethyl methacrylate, oleyl methacrylate, and diethylaminoethyl methacrylate which are quaternized with dimethyl sulfate, and the like. Representative copolymers of the second type include those of alkyl acrylates and ethylene such as A-C Copolymer 540 ® {Allied Signal, Inc., Morristown, N.J.}, and those of acrylic acid and vinyl alcohol such as Hydagen F ® {Henkel Corporation, Hoboken, N.J.}. Poly(methyl methacrylate) is a preferred (meth)acrylate polymer.

The amount of topically acceptable polymer added to the flexible collodion composition is at least the minimum amount sufficient to increase the resilience of the film formed. Generally, this amount will be from about 0.05% to about 10% by weight of the total composition. While it is recognized that the addition of polymer in amounts greater than about 10% will still achieve the desired result of increased resilience, a point is reached at which the addition of further amounts of polymer is economically unrewarding due to the minimal additional benefit afforded. Generally, the amount of polyalkylene added is from about 0.05 to about 5% by weight of the total composition, preferably from about 0.1 to about 1%. The amount of (meth)acrylate homo- or copolymer typically added is from about 0.05 to about 10% by weight of the total composition, preferably from about 0.1 to about 1%.

The resulting flexible collodion composition exhibits an increased resilience in the film formed. The film thus shows increased durability and resistance to "rub-off" or abrasion, increased tenacity, increased flexibility, and increased occlusivity. The above attributes imparted by the polymer to the film formed lead to (1) improved compliance, since the film formed is less "sloppy" than the film formed by conventional flexible collodion compositions, and (2) improved therapeutic efficacy, as the film formed will remain intact where applied for an increased duration and the improved occlusivity will enhance the penetration of any therapeutic agent present in the composition.

One particular area of pharmaceuticals where flexible collodion compositions are employed and thus where the present invention is particularly useful is in the treatment of hyperkeratosis, a condition characterized by an overgrowth of the horny layer of the skin. Hyperkeratotic conditions include corns, calluses and warts.

Keratolytic agents are used topically in the treatment of hyperkeratosis and act by softening and destroying the stratum corneum layer of the skin, thereby enhancing desquamation at the site of application. Salicylic acid is a commonly used keratolytic agent. Other keratolytic agents include ascorbic acid, calcium pantothenate, glacial acetic acid, lactic acid, podophyllum resin, and zinc chloride.

Salicylic acid is keratolytic at about 5% by weight of the total composition. While higher concentrations of salicylic acid can be used, generally no more than about 40% by weight of salicylic acid is desirable as higher concentrations are excessively corrosive or caustic.

Keratolytic agents are typically applied topically to the hyperkeratotic lesion in a film forming fluid composition including flexible collodion. "Fluid" means capable of flowing and thus includes both liquid and gel compositions.

Keratolytic agents generally are formulated in flexible collodion compositions because the film-forming property of the flexible collodion provides two important advantages. First, the application of flexible collodion to a hyperkeratotic lesion is far more precise than the application of a runny solution due to the ability of the flexible collodion to rapidly dry and form a film. This property is important as it minimizes the discomfort resulting from inadvertent application of a keratolytic agent to the healthy, normal tissue surrounding the hyperkeratotic lesion. Second, the occlusive film formed by the flexible collodion prevents the evaporation of moisture from the area. The increased retention of moisture by the tissues enhances permeation of the keratolytic agent, maceration and sloughing.

Thus in one aspect the present invention is useful in the treatment of hyperkeratosis. A film-forming fluid composition including a keratolytic agent such as salicylic acid, flexible collodion and a topically acceptable polymer according to the present invention in an amount sufficient to increase the resilience of the film formed will exhibit the improved compliance and improved therapeutic efficacy discussed above.

By incorporating a local anesthetic in compounds used for traditional wart therapy, the present invention alleviates the localized discomfort and irritation often associated with the application of keratolytics to the skin.

Local anesthetics include, but are not limited to, esters of benzoic acid such as benzocaine, procaine, tetracaine, and chloroprocaine, and amides such as bupivacaine, dibucaine, lidocaine, mepivacaine, prilocaine, and etidocaine.

The amount of local anesthetic present will be that which is effective in achieving localized anesthesia in the area to which the anti-wart agent is applied, generally from about 0.5% to about 15% or more and preferably from 1% to 10% by weight of composition. For lidocaine, for example, the effective range is from about 0.5% to about 4%. With benzocaine, the effective range is from about 5% to about 25%.

In another embodiment the present invention comprises a salt, the anion of which is the salicylic acid, lactic acid or chloroacetic acid anion and the cation of which is the protonated form of benzocaine, procaine, tetracaine, chloroprocaine, bupivacaine, dibucaine, lidocaine, mepivacaine, prilocaine, or etidocaine.

The salt can be formed either in situ, i.e. by the contemporaneous application to the skin of an acidic keratolytic agent and a basic local anesthetic, or prior to application when these two elements are brought together in a pharmaceutical preparation.

The present invention also includes the method of treating warts which comprises applying to the wart a composition comprising a therapeutically effective amount of at least one topical keratolytic agent such as salicylic acid, lactic acid, or chloroacetic acid and an anesthetically effective amount of a local anesthetic such as benzocaine, procaine, tetracaine, chloroprocaine, bupivacaine, dibucaine, lidocaine, mepivacaine, prilocaine, or etidocaine.

Historically, a problem has been encountered with compositions of salicylic acid and flexible collodion. During normal usage by a patient or consumer, the salicylic acid tends to crystallize out of solution, both on the applicator and the mouth of the container. The terms "crystallize" or "crystallization" refer to the separation of solid from the solution which, for present purposes, is synonymous with precipitation. The crystallization of the salicylic acid from solution decreases the concentration of salicylic acid in solution which correspondingly decreases the keratolytic activity of the composition. The addition of lactic acid to formulations of salicylic acid in flexible collodion has been found to retard the formation of crystals, thereby yielding formulations acceptable for commercialization. Such formulations are marketed under the product names Duofilm ® {Stiefel Laboratories, Coral Gables, Fla.}, Wart-Off ® {Pfizer, Inc., New York, N.Y.}, and Tinamed ® {Durham Pharmacal, Oak Hill, N.Y.}.

Surprisingly, it has been discovered that a film-forming composition including salicylic acid dissolved in flexible collodion can be improved by the inclusion of a topically acceptable crystallization inhibitor. The crystallization inhibitor is at least one mono- or polyester and/or ether.

Esters are conventionally defined in terms of an acid portion and an alcohol portion. Typical acids which can serve as the acid portion of the ester-type crystallization inhibitor include alkanoic acids, hydroxyalkanoic acids, alkenoic acids, and hydroxyalkenoic acids, each having from two to twenty carbon atoms and being either straight chain or branched, and benzoic acids. Examples of suitable alkanoic acids include acetic acid, isobutyric acid, pelargonic acid, isononanoic acid and isostearic acid. Suitable hydroxyalkanoic acids include lactic acid, hydroxybutyric acid, and hydroxypentanoic acid. Suitable alkenoic acids include acrylic acid, crotonic acid, and oleic acid. Ricinoleic acid is an example of a suitable hydroxyalkenoic acid.

Typical alcohols which can serve as the alcohol portion of the ester-type crystallization inhibitor include monohydroxyalkanes, polyhydroxyalkanes, poly(alkanediol)s, and saccharides. Examples of suitable monohydroxyalkanes include ethanol, propanol, butanol, isobutanol, octanol, and isostearol. Suitable polyhydroxyalkanes include ethylene glycol, propylene glycol, and glycerol. Poly(alkanediol)s include the polyethylene glycols. Examples of suitable saccharides include the disaccharides, i.e., sucrose, maltose, and lactose.

Typical mono- or polyester crystallization inhibitors thus include ethyl acetate, ethyl acrylate, ethyl pelargonate, ethyl lactate, propyl acetate, octyl isononanoate, isostearyl isostearate, isobutyl benzoate, isostearyl benzoate, propylene glycol isostearate, propylene glycol dipelargonate, polyethylene glycol dilaurate, castor oil, and sucrose acetate isobutyrate.

The crystallization inhibitor also can be one or more ethers. Ethers can be defined as consisting of a first group and a second group linked through an ethereal oxygen atom. Suitable first groups include alkyl groups and phenyl groups. Suitable alkyl groups are typically from one to twenty carbon atoms, such as methyl, ethyl, propyl, stearyl, and the like, and can be straight chain or branched. The phenyl groups can be unsubstituted or substituted with alkyl groups, typically of one to ten carbon atoms, which also can be straight chain or branched.

Suitable second groups are hydroxyalkyl, polyhydroxyalkyl, and alkanediol groups. Typical hydroxyalkyl groups include hydroxyethyl, hydroxypropyl, and hydroxybutyl. Suitable polyhydroxyalkyl groups include dihydroxyalkyls of one to ten carbon atoms such as dihydroxypropyl and dihydroxybutyl. Suitable poly(alkanediol)s include the polyethylene glycols. Examples of suitable ether-type crystallization inhibitors thus include ethoxyethanol, polyethylene glycol stearyl ether, octoxynol, and nonoxynol.

Preferred topically acceptable crystallization inhibitors include propylene glycol dipelargonate, ethyl lactate, and castor oil, either alone or in combination. Mixtures of ethyl lactate and castor oil or ethyl lactate alone are most preferred.

The amount of topically acceptable crystallization inhibitor utilized is an amount sufficient to suppress the crystallization of dissolved salicylic acid from the flexible collodion solution. Generally, the amount of crystallization inhibitor sufficient to suppress the crystallization of dissolved salicylic acid from the flexible collodion composition is from about 1 to about 60% by weight of the total composition. Amounts of crystallization inhibitor greater than 60% will still suppress crystallization. Economic factors, however, outweigh the minimal benefit gained by the addition of further amounts of crystallization inhibitor.

Compositions of the present invention can also include topically acceptable pharmaceutical excipients, such as solvents, diluents, thickeners, etc.

Typical liquid compositions for the topical treatment of hyperkeratosis embodied by the present invention include from about 5 to about 40% by weight of the total composition of salicylic acid, at least about 50% by weight of the total composition of flexible collodion, and from about 15 to about 45% by weight of the total composition of ethyl lactate. The amount of salicylic acid is preferably from about 15 to about 30%, and most preferably about 17% or about 27% by weight of the total composition. Additionally, such liquid compositions typically can include from 1 to 15%, preferably about 3% by weight of the total composition of castor oil. (The amount of castor oil present as a crystallization inhibitor is expressed in excess of the castor oil contained in flexible collodion.)

Typical gel compositions for the topical treatment of hyperkeratosis embodied by the present invention include from about 5 to about 40% by weight of the total composition of salicylic acid, from about 20 to about 60% by weight of the total composition of flexible collodion, and from about 5 to about 25% by weight of the total composition of ethyl lactate. The amount of salicylic acid is preferably from about 15 to about 30%, and most preferably about 17% or about 27%, by weight of the total composition.

The following examples will serve to further typify the nature of this invention. These examples, however, should not be construed as being a limitation on the scope of the invention, which scope is defined solely by the appended claims.

EXAMPLE 1

A flexible collodion composition is prepared by first adding 15.0 g of ethyl lactate to 64.9 g of flexible collodion while stirring. Stirring is continued until the mixture is uniform. Next, 3.0 g of castor oil are added, followed by 0.1 g of polybutylene (Indopol® L-50). Finally, 17.0 g of salicylic acid are slowly dissolved in the mixture with stirring. About 100.0 g of a clear pale-yellow liquid are produced.

EXAMPLE 2

While stirring, 45.1 g of alcohol are added to 21.8 g of flexible collodion. To this mixture are added 5.0 g of ethyl lactate, followed by 0.1 g of polybutylene (Indopol® L-50). Once the mixture is uniform, 27.0 g of salicylic acid are slowly added, stirring until completely dissolved. With rapid agitation, 1.0 g of hydroxyethyl cellulose is added and the mixture is allowed to sit overnight. About 100.0 g of clear gel are produced.

EXAMPLE 3

Fifteen grams of ethyl lactate are added to 64.8 g of flexible collodion, stirring until uniform. To this mixture are added 3.0 g of castor oil. Then 0.1 g of polybutylene (Indopol® L-50) is added. While stirring, 17.0 g of salicylic acid are added and dissolved in the mixture. Finally, 0.1 g of polymethyl methacrylate is added to the mixture, yielding 100.0 g of a clear, pale-yellow liquid composition.

EXAMPLE 4

In order to produce 100.0 g of a liquid flexible collodion composition, 10.0 g of ethyl alcohol and 6.0 g of propylene glycol dipelargonate are stirred, one at a time, into 67.0 g of flexible collodion. When uniform, 17.0 g of salicylic acid are added slowly to the mixture which is stirred until the salicylic acid is completely dissolved. The product is clear and pale-yellow.

EXAMPLE 5

A flexible collodion composition is produced by taking 21.8 g of flexible collodion and adding to it 45.0 g of alcohol, followed by 5.0 g of ethyl lactate, while stirring. To this mixture, 0.1 g of polybutylene (Indopol ® L-50) is added and the mixture is stirred until uniform. Next, 27.0 g of salicylic acid are slowly added while stirring. Once the salicylic acid is completely dissolved, 1.0 g of hydroxyethyl cellulose and 0.1 g of polymethyl methacrylate are added with rapid agitation. After sitting overnight, the mixture yields 100.0 g of a clear gel product.

EXAMPLE 6

The procedure in Example 2 is followed, except the following amounts are used: 32.0 g of alcohol, 44.9 g of flexible collodion, 5.0 g of ethyl lactate, 0.1 g of polybutylene (Indopol ® L-50), 17.0 g of salicylic acid, and 1.0 g of hydroxyethyl cellulose. The procedure yields 100.0 g of a clear gel composition.

EXAMPLE 7

The procedure in Example 2 is followed, except the following amounts are used: 51.4 g of alcohol, 25.0 g of flexible collodion, 5.0 g ethyl lactate, 0.1 g of polybutylene (Indopol ® L-50), 17.0 g of salicylic acid, and 1.5 g of hydroxyethyl cellulose. The procedure yields 100.0 g of a clear gel composition.

EXAMPLE 8

A flexible collodion composition is prepared by adding 45.1 g of alcohol and 5.0 g of ethyl lactate, one at a time, to 21.9 g of flexible collodion while stirring. To this mixture are slowly added 27.0 g of salicylic acid, and the mixture is stirred until the salicylic acid is completely dissolved. Hydroxyethyl cellulose in the amount of 1.0 g is added with rapid agitation and the product is allowed to sit overnight, yielding 100.0 g of a clear gel.

EXAMPLE 9

In order to produce 100.0 g of a flexible collodion composition, 15.0 g of ethyl lactate, followed by 3.0 g of castor oil, are mixed with 65.0 g of flexible collodion. Then, 17.0 g of salicylic acid is slowly dissolved into this mixture. The product is a clear, pale-yellow liquid.

EXAMPLE 10

The procedure of Example 8 is followed, except the following amounts are used: 51.7 g of alcohol, 5.0 g of ethyl lactate, 25.0 g of flexible collodion, 17.0 g of salicylic acid, and 1.3 g of hydroxyethyl cellulose. About 100.0 g of clear gel are produced.

EXAMPLE 11

One hundred grams of a liquid composition is produced by mixing 16.5 g of ethyl lactate with 66.5 g of flexible collodion, and subsequently dissolving 17.0 g of salicylic acid in this mixture. The final product is clear and pale-yellow in color.

EXAMPLE 12

A flexible collodion composition is prepared by first adding 15.0 g of ethyl lactate to 54.9 g of flexible collodion while stirring. Stirring is continued until the mixture is uniform. Next, 3.0 g of castor oil is added, followed by 0.1 g of isobutylene-butene copolymer. Finally, 17.0 g of salicylic acid and 10.0 g of benzocaine are slowly dissolved in the mixture while stirring. About 100.0 g of clear pale-yellow liquid is produced.

EXAMPLE 13

| Ingredient | % Total Comp. |
| --- | --- |
| Flexible Collodion | 21.800 |
| Salicylic Acid | 17.000 |
| Benzocaine | 10.000 |
| Hydroxypropyl Cellulose | 1.200 |
| Ethanol (SD alcohol 40B) | q.s. to 100.000 |

The foregoing ingredients are combined in a suitable container and thoroughly mixed to form a uniform preparation. A small amount of the preparation is applied directly to the wart loci. The preparation dries to form a film on the skin.

EXAMPLE 14

| Ingredient | % Total Comp. |
| --- | --- |
| Salicylic Acid | 27.000 |
| Flexible Collodion | 21.800 |
| Lactic Acid | 5.000 |
| Hydroxypropyl Cellulose | 1.500 |
| Lidocaine | 1.000 |
| Ethanol (SD alcohol 40B) | q.s. to 100.000 |

The foregoing ingredients are combined in a suitable container and thoroughly mixed to form a uniform preparation. A small amount of the preparation is applied directly to the wart loci. The preparation dries to form a film.

EXAMPLE 15

| Ingredient | % Total Comp. |
| --- | --- |
| Flexible Collodion | 24.500 |
| Chloroacetic Acid | 17.000 |
| Lactic Acid | 5.000 |
| Hydroxypropyl Cellulose | 3.000 |
| Lidocaine | 2.000 |
| Ethanol (SD alcohol 40B) | q.s. to 100.000 |

The foregoing ingredients are combined in a suitable container and thoroughly mixed to form a uniform preparation. A small amount of the preparation is applied directly to the wart loci. The preparation dries to form a film.

EXAMPLE 16

| Ingredient | % Total Comp. |
| --- | --- |
| Flexible Collodion | 66.000 |
| Salicylic Acid | 16.500 |
| Lactic Acid | 16.500 |
| Tetracaine | 1.000 |

The foregoing ingredients are combined in a suitable container and thoroughly mixed to form a uniform preparation. A small amount of the preparation is applied directly to the wart loci. The preparation dries to form a film.

What is claimed is:

1. A fluid film-forming composition, comprising:
   (A) flexible collodion, comprising a solution of nitrocellulose in a mixture of ethyl ether and ethanol, to which solution camphor and castor oil have been added;
   (B) a keratolytic agent; and
   (C) an additive which is:
   (1) a homo- or co-polymer selected from the group consisting of: (i) a polyalkylene; and (ii) a (meth)acrylate; in an amount sufficient to increase film resilience;
   (2) a crystallization inhibitor selected from the group consisting of: (i) a mono- or poly-ester, having an acid portion which is an alkanoic, hydroxyalkanoic, alkenoic, or hydroxyalkenoic acid or benzoic acid, and an alcohol portion which is a monohydroxyalkane, polyhydroxyalkane, poly(alkanediol) or saccharide; and (ii) an ether in which an alkyl, phenyl or alkyl-substituted phenyl group is linked by an ethereal oxygen atom to a hydroxyalkane, poly(alkanediol) or polyhydroxyalkyl group; in an amount sufficient to inhibit crystallization of the keratolytic agent; or
   (3) mixtures thereof.

2. The composition of claim 1, in which salicylic acid comprises about 15 to about 30 percent by weight.

3. The composition of claim 1, in which salicylic acid comprises about 17 percent by weight.

4. The composition of claim 1, in which ethyl lactate comprises about 15 to about 45 percent by weight.

5. The composition of claim 1, in which the castor oil of (D) comprises about 1 to about 15 percent by weight.

6. A method for the topical treatment of keratosis, comprising applying the composition of claim 1 to skin.

* * * * *

UNITED STATES PATENT AND TRADEMARK OFFICE
CERTIFICATE OF CORRECTION

PATENT NO. : 5,433,950
DATED : July 18, 1995
INVENTOR(S) : Karl F. Popp

It is certified that error appears in the above-indentified patent and that said Letters Patent is hereby corrected as shown below:

Column 9,
Claim 1 should read as follows:

1. A liquid film-forming composition, comprising:

(A) at least about 50 percent by weight of flexible collodion, comprising a solution of nitrocellulose in a mixture of ethyl ether and ethanol, to which solution camphor and castor oil have been added;

(B) about 5 to about 40 percent by weight of salicylic acid;

(C) about 0.05 to about 5 percent by weight of a polybutylene; and (D) about 1 to about 60 percent by weight of a crystallization inhibitor comprising ethyl lactate and castor oil.

Signed and Sealed this

Nineteenth Day of November, 1996

*Attest:*

BRUCE LEHMAN

*Attesting Officer*     *Commissioner of Patents and Trademarks*